United States Patent
Zanelli et al.

(10) Patent No.: US 9,216,831 B2
(45) Date of Patent: Dec. 22, 2015

(54) METHOD AND PLANT FOR FILLING A BOTTLE WITH A RADIOACTIVE FLUID-BASED MIXTURE

(75) Inventors: Alessia Zanelli, Faenza (IT); Stefano Bosi, Faenza (IT)

(73) Assignee: Comecer S.p.A. (IT)

(*) Notice: Subject to any disclaimer, the term of this patent is extended or adjusted under 35 U.S.C. 154(b) by 920 days.

(21) Appl. No.: 13/299,925

(22) Filed: Nov. 18, 2011

(65) Prior Publication Data
US 2012/0298252 A1    Nov. 29, 2012

(30) Foreign Application Priority Data
Nov. 18, 2010    (IT) .............................. BO2010A0689

(51) Int. Cl.
| | |
|---|---|
| *B65B 3/14* | (2006.01) |
| *B65B 3/00* | (2006.01) |
| *A61K 51/00* | (2006.01) |
| *G21F 5/015* | (2006.01) |
| *G21G 1/00* | (2006.01) |

(52) U.S. Cl.
CPC . *B65B 3/14* (2013.01); *A61K 51/00* (2013.01); *B65B 3/003* (2013.01); *B65B 3/006* (2013.01); *G21F 5/015* (2013.01); *G21G 1/0005* (2013.01)

(58) Field of Classification Search
CPC .......... B65B 3/003; B65B 3/006; B65B 3/14; A61K 51/00
USPC .......... 141/37, 39, 63, 67, 104–105, 302, 18, 141/89, 91, 83; 250/428, 432 R, 431
See application file for complete search history.

(56) References Cited

U.S. PATENT DOCUMENTS 4,296,785 A * 10/1981 Vitello et al. ................. 141/105
2011/0178359 A1 * 7/2011 Hirschman et al. ............... 600/4

FOREIGN PATENT DOCUMENTS

| JP | 2005343798 | 12/2005 |
|---|---|---|
| JP | 2006349649 | 12/2006 |
| WO | WO 2008/083313 | 7/2008 |

OTHER PUBLICATIONS

Italian Search Report in IT Appln. No. BO2010A000689, dated Jul. 27, 2011 [2 pgs.].

* cited by examiner

*Primary Examiner* — Timothy L Maust
*Assistant Examiner* — Timothy P Kelly
(74) *Attorney, Agent, or Firm* — Davidson Berquist Jackson & Gowdey LLP

(57) ABSTRACT

The method provides:
a first step, in which a radioactive fluid is conveyed from a source to a container;
a second step, during which inert gas under pressure is conveyed towards the container; and
a third step, during which, due to the action of the inert gas, the radioactive fluid is conveyed from the container to a bottle.

5 Claims, 1 Drawing Sheet

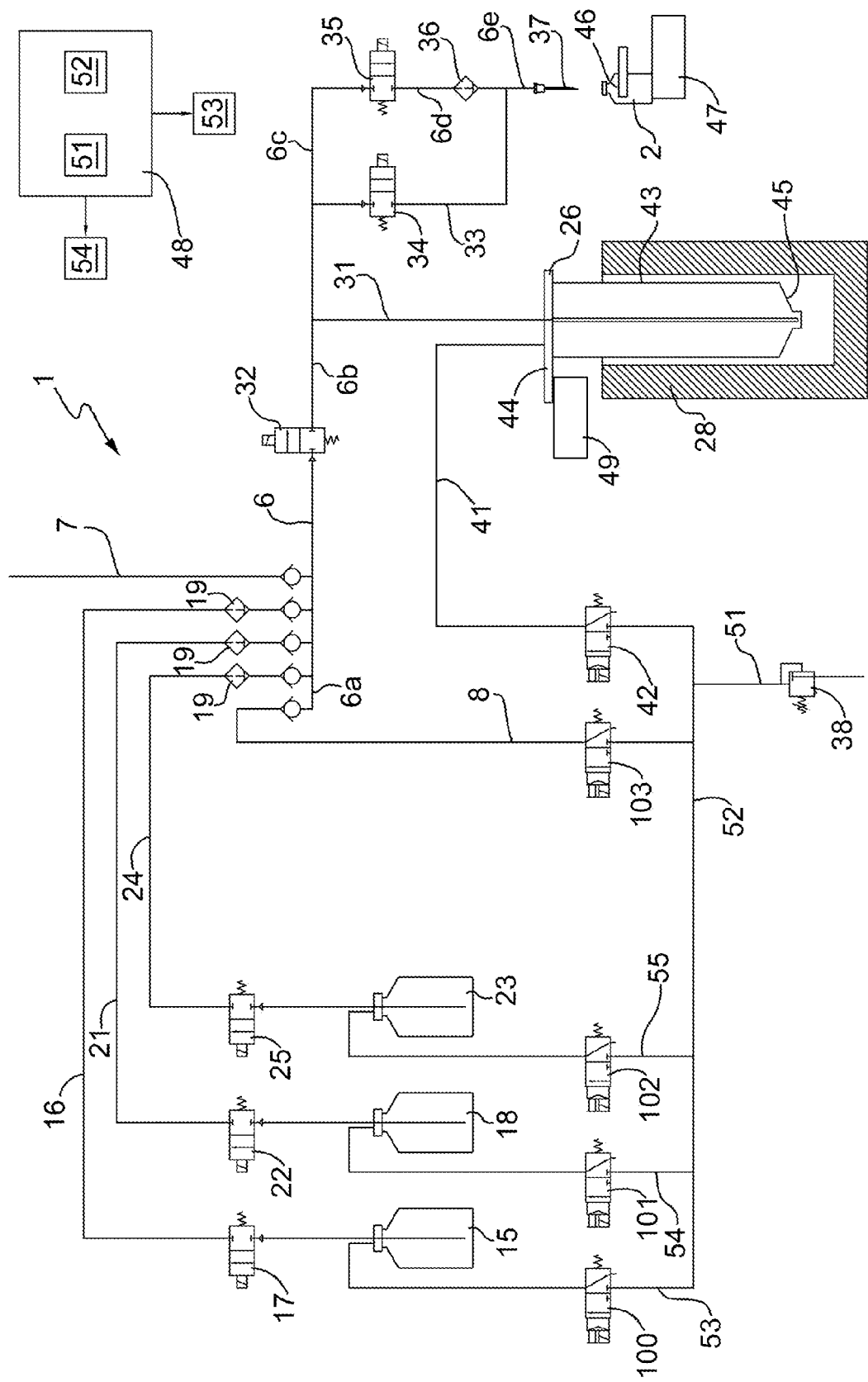

METHOD AND PLANT FOR FILLING A BOTTLE WITH A RADIOACTIVE FLUID-BASED MIXTURE

The present invention relates to a method for filling a bottle with a radioactive fluid-based mixture, to a plant for filling a bottle with a radioactive fluid-based mixture and to a kit used in said plant.

BACKGROUND OF THE INVENTION

As it is known, a plant is currently used for filling a bottle with radioactive material, providing a tank with radioactive fluid, a duct which conveys the fluid towards a container, a second duct which conveys the fluid from the container to the bottle and a peristaltic pump applied on such second duct which controls the conveying of the fluid towards the bottle.

The main problem with the above-described plant relates to the difficulty in controlling the flow rate of the fluid conveyed by means of the action of the peristaltic pump. Indeed, as known, the peristaltic pump is nothing more than a rotating projection caused by the action of an electric motor which periodically pushes on the duct so that the fluid in the duct is encouraged to cross the duct. It is apparent that the only means which allow the flow rate of the fluid in the duct to be regulated consist in regulating the speed of rotation of the projection which pushes on the duct, and as known, such regulation is coarse. Furthermore, the above-described plant has further problems if further fluids, such as e.g. a buffer fluid, are to be added to the radioactive fluid before being conveyed towards the bottle. Lastly, it is worth noting that making the aforesaid plant even more problematic to use is that the different ducts and the above-mentioned shielded container are to be subjected to a thorough washing by means of e.g. water and/or ethanol. The use of peristaltic pumps which, as is known, are apparatuses which allow conveying fluids under low pressure, is capable of achieving perfect and thorough washing.

SUMMARY OF THE INVENTION

The object of the present invention is to create a method for filling a bottle with a radioactive fluid-based mixture which does not have the above-mentioned drawbacks.

A further object of the present invention is to make a plant which implements the aforesaid method and a kit which can be used in such a plant.

Based on the present invention, a method is created for filling a bottle with a radioactive fluid as indicated in claim 1.

Based on the present invention, a plant is also made for filling a bottle with a radioactive fluid as indicated in claim 7.

Based on the present invention, a kit is also created for filling a bottle with a radioactive fluid as indicated in claim 17.

BRIEF DESCRIPTION OF THE DRAWING

The following example, with the aid of the accompanying FIGURE, serves the purpose of non-limiting example to better comprehend the invention, in which numeral 1 indicates a plant as a whole for filling a bottle 2 with a radioactive fluid.

DETAILED DESCRIPTION OF THE INVENTION

Plant 1 comprises:
a main duct 6;
a duct 7 adapted to establish a hydraulic communication between a module containing a radiopharmaceutical and the main duct 6;
a tank 15 containing a buffer fluid;
a duct 16 adapted to establish a hydraulic communication between tank 15 and the main duct 6 and along which a valve 17 is installed, adapted to act, from the outside, on duct 16 to open and close the passage of the buffer fluid;
a tank 18 containing a first washing fluid, such as e.g. water;
a duct 21 adapted to establish a hydraulic communication between tank 18 and the main duct 6 and along which a valve 22 is installed, adapted to act, from the outside, on duct 21 to open and close the passage of the first washing fluid;
a tank 23 containing a second washing fluid, such as e.g. ethanol;
a duct 24 adapted to establish a hydraulic communication between tank 23 and the main duct 6 and along which a valve 25 is installed, adapted to act, from the outside, on duct 24 to open and close the passage of the second washing fluid;
a container 26 installed inside a gauger 28 which, as is known, is a device adapted to measure the radioactivity value of the liquid in container 26;
a device 49 adapted to measure the weight of container 26; and
a duct 31 adapted to establish a communication between container 26 and the main duct 6.

A respective filter 19 is installed along ducts 16, 21 and 24.

Plant 1 comprises an automatic pressure regulator 38, which is connected upstream to an inert gas source and downstream, by means of a duct 51, to a duct 52, from which the following originate:
a duct 53, which connects duct 52 with tank 15 and along which a solenoid valve 100 is installed, which is normally closed and which, when opened, is adapted to put tank 15 under pressure, so as to let the buffer fluid flow towards the main duct 6 through duct 16;
a duct 54, which connects duct 52 with tank 18 and along which a solenoid valve 101 is installed, which is normally closed and which, when opened, is adapted to put tank 18 under pressure, so as to let the first washing fluid flow towards the main duct 6 through duct 21;
a duct 55, which connects duct 52 with tank 23 and along which a solenoid valve 102 is installed, which is normally closed and which, when opened, is adapted to put tank 23 under pressure, so as to let the second washing fluid flow towards the main duct 6 through duct 24;
a duct 8, which connects duct 52 to an end of the main duct 6 and along which a solenoid valve 103 is installed, which is normally closed and which, when opened, is adapted to let the inert gas flow towards the main duct 6; and
a duct 41, which connects duct 52 to container 26 and along which a solenoid valve 42 is installed, which is normally closed and which, when opened, is adapted to let the inert gas flow towards container 26.

With reference to the accompanying drawing, duct 6 has, in sequence:
a first section 6a, which is joined, in sequence, by ducts 8, 24, 21, 16 and 7, each of them by means of a check valve 5;
a second section 6b, which follows the first section 6a, there being installed between the two sections a valve 32, which is adapted to act, from the outside, on duct 6 to open and close the passage of the fluid circulating in duct 6, section 6b being in communication with container 26 by means of duct 31;
a third section 6c, in which a branch duct 33 originates from the main duct 6, there being installed along said branch duct 33 a valve 34, which is adapted to act, from the outside, on duct 33 to open and close the passage of the fluid circulating in duct 33;

a fourth section 6d, which is parallel to the branch duct 33 and along which a valve 35 is installed, which is adapted to act, from the outside, on duct 6 to open and close the passage of the fluid circulating in duct 6, and which terminates on a filter 36; and a fifth and last section 6e, which is joined, at first, by the branch duct 33, and at the end of which a nozzle 37 is installed, from which the conveyed fluid can be released.

Container 26 comprises a cup-shaped body 43 and a cover 44; the cup-shaped body 43 preferably being cylindrical. Duct 31 enters the cup-shaped body 43 through a hole made in the middle zone of cover 44 and extends until it is close to a bottom wall 45 of the cup-shaped body 43. Duct 41 joins in a semi-central zone of cover 44.

Lastly, plant 1 comprises:

a vial moving system 46 (diagramatically illustrated) adapted to transfer bottle 2 from a filling station defined at nozzle 37 to a successive packing and storing station;

a device 47 (diagramatically illustrated) for measuring the weight of bottle 2 installed at the aforesaid filling station; and an electronic control unit 48, which is adapted to control the different organs of plant 1 and in particular, the solenoid valves 100, 101, 102, 103, 42, the valves 17, 22, 25, 32, 34 and 35 5 and 42, the automatic pressure regulator 38 and the moving system 46, and is adapted to receive the data measured by the devices 47 and 49 and by gauger 28.

The electronic control unit 48 is provided with a memory block 51, in which all the recipes are stored of the fluid used to fill the bottle 2, and with a comparison block 52 for comparing the data measured in the plant 1 with the data set by means of a data setting block 53 connected to the electronic control unit. Lastly, the control unit 48 is adapted to control a block 54 which is adapted to display all the data involved in plant 1.

Plant 1 comprises a plurality of fixed organs, such as e.g. the ducts 7, 8, 16, 21, 24, 41, 15, 18 and 23, the tanks 15, 18 and 23, gauger 28, the devices 47 and 49, the moving system 46, the control unit 48 and a kit, which performs a series of operations and which is periodically replaced with a new kit.

It is apparent that the kit consists of the main duct 6 with nozzle 37 and filter 36, of the ducts 31 and 33 and of container 26.

The method for filling bottle 2 with a radioactive fluid-based mixture provides:

a step in which a series of data is set up by means of block 53, such as the mixture of the fluid to be conveyed into bottle 2, and hence the quantity of radioactive fluid to be conveyed towards container 26 and the quantity of buffer fluid to be mixed with such a radioactive fluid;

a step in which the quantity is set up of said mixture to be conveyed from container 26 to bottle 2;

a step in which valve 32 is closed when all the fluid has been emitted into container 26 (naturally according to the volume of the latter);

a step in which valve 17 and the solenoid valve 100 are opened for a time such as to convey the pre-set quantity of buffer fluid from tank 15 to container 26 (device 49 being adapted to report the weight to the control unit 48 and hence the volume reached in container 26 to close valve 17);

a mixing step in which, with valve 32 open and valves 34 and 35 closed, the solenoid valve 103 is opened so that the inert gas enters container 26 to perform the mixing of the liquid contained therein;

a step in which, due to the action of the inert gas, the mixture contained inside container 26 is conveyed through the main duct 6 towards nozzle 37 and from the latter into bottle 2;

a step in which, due to the measuring by device 47, the solenoid valve 42 and valve 35 are closed once the quantity of selected mixture has been reached in bottle 2; and a step in which the moving system 46 is controlled, which determines the translation of the filled bottle 2 towards the packing station and the translation of an empty bottle 2 towards the filling station.

The method the object of the present invention periodically comprises:

a step in which the moving system 46 brings a first sample bottle 2 into the filling station;

a step in which such a first sample bottle 2 is filled, according to the above-described methods, with a pre-selected quantity of mixture, quantity measured by device 47;

a step in which the moving system 46 brings a second sample bottle 2 into the filling station;

a step in which section 6d is bypassed by closing valve 35 and opening valve 34 so as to fill the second sample bottle 2 through the branch duct 33 with the same quantity of mixture used for the first sample bottle 2;

a step in which the quantity of mixture contained in the second sample bottle 2 is measured by means of device 47; and a step in which the quantity is compared of mixture contained in the two samples bottles 2 measured by device 47.

In essence:

first, a selected quantity of mixture is conveyed towards the sample bottles 2, a first conveying through section 6e of the main duct 6 and a second conveying through the branch duct 33;

then is measured the actual quantity of mixture which fills the two sample bottles 2; and lastly, it is compared the actual quantity of mixture contained in the two sample bottles 2.

Thereby, it is possible to control the effectiveness of filter 36 and for this reason, all these data are then displayed in block 54 so that the appointed personnel is informed on the possibility of having to change filter 36 or having to change the kit.

Moreover, the kit is periodically washed.

Such a washing provides:

a step in which the solenoid valves 100, 101, 102, 103 and 42 and the valves 34, 35, 17, 22 and 25 are closed;

a step in which the selection of the washing fluid to use is made from among those contained in the tanks 18 and 23, or whether or not to use a mixture of such washing fluids by opening the solenoid valve 22 and/or 25;

a step in which container 26 is filled with the washing fluid;

a step in which the valves 22, 25 and 32 are closed;

a step in which nozzle 37 is connected with a tube which is connected to a discharge station, or a bottle 2 is brought into the filling station that is then sent towards the discharge station at the end of the operation; and a step in which valve 42 is opened so that inert gas enters container 26, and valves 34 and 35 are opened, either simultaneously or in succession, so that the washing fluid is conveyed towards nozzle 37.

Thereby, the kit is periodically subjected to proper and effective washing.

The numerous advantages achieved with the present invention are apparent from the above description.

In particular, a method and a plant were created for filling a bottle with a radioactive fluid-based mixture, which automatically perform such a filling. Moreover, all the filling steps are controlled and extremely accurate filling is obtained because it is possible to control the quantity of fluids conveyed by means of the solenoid valves, the valves and the pressure regulator, and furthermore the quantity of mixture emitted into the bottle is measured moment by moment. It is worth noting that not only is accurate filling controlled, but the effectiveness is also controlled of certain organs in the kit such as e.g. filter 36. It is also worth noting that the action of the inert gas under pressure not only conveys the mixture but also obtains an effective homogenization of the components in the mixture. Lastly, it is worth noting that washing the aforesaid kit is periodically and always automatically obtained with the same plant.

The invention claimed is:

1. A method for filling a bottle with a radioactive fluid-based mixture comprising the steps of:
   a first step, in which a radioactive fluid is conveyed from a source to a container;
   a second step, during which inert gas under pressure is conveyed towards said container; and
   a third step, during which, due to the action of the inert gas, the radioactive fluid is conveyed from the container to said bottle, and;
   wherein between said second and third steps, an intermediate step, during which a buffer fluid is conveyed towards said container, so as to be mixed with the radioactive fluid, thus obtaining a radioactive fluid-based mixture which is then conveyed, during said third step, towards and into the bottle.

2. The method according to claim 1, further including a step, which precedes said first step and during which a series of data are set, of selecting among different said radioactive fluids with different radioactive concentrations and a quantity of said buffer fluid to be mixed with said radioactive fluid inside said container, and a step, which also precedes said first step and during which a quantity of the mixture to be conveyed from said container to said bottle is set.

3. The method according to claim 2 further including a fourth step, in which bottle filling is interrupted once the selected quantity of said mixture introduced into said bottle has been reached and detected.

4. The method according to claim 3 further including:
   a fifth step, in which, once the filling phase is ended, at least one washing fluid is conveyed from a suited third tank towards said container;
   a sixth step, during which inert gas under pressure is conveyed towards said container; and
   a seventh step, during which, due to the action of the inert gas, the washing fluid is conveyed from said container to a discharge station.

5. The method according to claim 1 wherein after said third step, a step, in which, at first, a sample bottle is filled with said mixture along a section of a main duct and, subsequently, a second sample bottle is filled along a branch duct, and an additional step of detecting the quantity of radioactive fluid conveyed, so that the effectiveness of the components which are installed along said section of the main duct; can be controlled.

* * * * *